(12) United States Patent
Bruns et al.

(10) Patent No.: US 8,143,275 B2
(45) Date of Patent: Mar. 27, 2012

(54) USE OF TRIAZOLOPYRIMIDINE DERIVATIVES AS MICROBICIDES

(75) Inventors: Rainer Bruns, Leverkusen (DE); Martin Kugler, Leichlingen (DE); Thomas Jaetsch, Cologne (DE); Hans-Ludwig Elbe, Wuppertal (DE); Dietmar Kuhnt, Burscheid (DE); Olaf Gebauer, Cologne (DE); Heiko Rieck, Langenfeld (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 12/982,927

(22) Filed: Dec. 31, 2010

(65) Prior Publication Data

US 2011/0098279 A1   Apr. 28, 2011

Related U.S. Application Data

(62) Division of application No. 10/147,224, filed on May 16, 2002, now Pat. No. 7,888,371.

(30) Foreign Application Priority Data

May 18, 2001   (DE) .................................. 101 24 208

(51) Int. Cl.
*A61K 31/47* (2006.01)

(52) U.S. Cl. ........................................ 514/310; 514/307
(58) Field of Classification Search .................. 514/307, 514/310
See application file for complete search history.

(56) References Cited

U.S. PATENT DOCUMENTS

| 5,252,582 | A | 10/1993 | Jautelat et al. |
| 5,593,996 | A | 1/1997 | Pees et al. |
| 5,985,883 | A | 11/1999 | Pees |
| 2004/0097522 | A1 | 5/2004 | Gebauer et al. |

FOREIGN PATENT DOCUMENTS

EP   336186 A2   10/1989

*Primary Examiner* — Zohreh Fay
(74) *Attorney, Agent, or Firm* — Nicanor A. Kohncke

(57) ABSTRACT

Use of compounds of the formula (I)

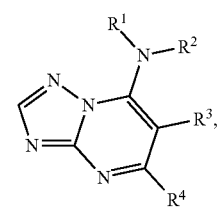

in which $R^1$, $R^2$, $R^3$ and $R^4$ are as defined in the description for protecting engineered materials.

4 Claims, No Drawings

USE OF TRIAZOLOPYRIMIDINE DERIVATIVES AS MICROBICIDES

CROSS REFERENCE TEXT

This application is a divisional of U.S. patent application Ser. No. 10/147,224 filed May 16, 2002, entitled "USE OF TRIAZOLOPYRIMIDINE DERIVATIVES AS MICROBICIDES", issued as U.S. Pat. No. 7,888,371 on Feb. 15, 2011, the contents of which are hereby incorporated by reference in their entirety.

BACKGROUND

The present application relates to the novel use of known triazolopyrimidine derivatives as microbicides for protecting engineered materials and to novel microbicidal compositions and novel microbicidal mixtures comprising these compounds.

Triazolopyrimidine derivatives whose pyrimidine ring is substituted in the 7-position by an amino group —$NR^1R^2$, in the 6-position by optionally substituted phenyl or naphthyl and in the 5-position by halogen or a radical —$NR^5R^6$ are already known from EP-A 550 113. The compounds described therein are suitable for protecting plants against attack by phytopathogenic fungi.

U.S. Pat. No. 5,985,883 also describes triazolopyrimidine derivatives substituted in the 6-position of the pyrimidine ring by 2,4,6-trichlorophenyl, which derivatives are suitable for protecting plants against attack by phytopathogenic fungi.

Surprisingly, it has now been found that the triazolopyrimidine derivatives described above have particularly good and broad microbicidal action against the microorganisms relevant for protecting engineered materials. This finding is particularly surprising since, firstly, the organisms in question are fundamentally different from the phytopathogenic fungi and, secondly, the protection of engineered materials requires fundamentally different standards of the substance with respect to its stability, its leaching properties, its color and its compatibility with other possible formulation auxiliaries.

Moreover, it has been found that the compounds to be used according to the invention are highly stable in engineered media.

SUMMARY

The invention relates to a method comprising treating an engineered material with a microbiocide compound of the formula (I)

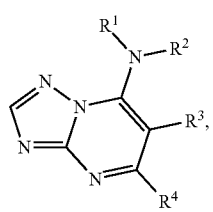

in which
$R^1$ represents optionally substituted alkyl, alkenyl, alkinyl, or cycloalkyl,
$R^2$ represents hydrogen or alkyl, or
$R^1$ and $R^2$ together with the nitrogen atom to which they are attached represent an optionally substituted heterocyclic ring,
$R^3$ represents optionally substituted aryl, and
$R^4$ represents hydrogen or halogens or their metal salts, acid addition compounds, N-oxides, (R)- and (S) isomers and, if compounds of the formula (I) contain a chiral centre, their racemates,
and thereby protecting the engineered material.

The invention also relates to a process for protecting an engineered material against attack and/or destruction by microorganisms, comprising allowing to act at least one compound of a formula (I) on the micro-organism or its habitat.

The invention also relates to a microbicidal composition comprising: (1) at least one compound of the formula (I), (2) at least one solvent or diluent and, optionally, processing auxiliaries and, optionally, further antimicrobially active compounds.

The invention also relates to an engineered material comprising at least one compound having formula (I).

These and other features, aspects, and advantages of the present invention will become better understood with reference to the following description and appended claims.

DESCRIPTION

The present invention provides the use of triazolopyrimidines of the formula (I)

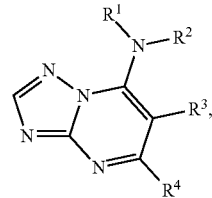

in which
$R^1$ represents optionally substituted alkyl, alkenyl, alkinyl, or cycloalkyl,
$R^2$ represents hydrogen or alkyl, or
$R^1$ and $R^2$ together with the nitrogen atom to which they are attached represent an optionally substituted heterocyclic ring,
$R^3$ represents optionally substituted aryl, and
$R^4$ represents hydrogen or halogen,
their metal salts, acid addition compounds, N-oxides, (R)- and (S) isomers and, if compounds of the formula (I) contain a chiral centre, their racemates, for protecting engineered materials.

For the purpose of the present invention, the alkyl radicals mentioned are straight-chain or branched and unsubstituted or substituted and contain 1 to 12 C atoms, in particular 1 to 8 C atoms and preferably 1 to 4 C atoms. Particularly preferred alkyl radicals are methyl, ethyl and propyl. The alkenyl and alkinyl radicals mentioned are in each case straight-chain or branched and in each case unsubstituted or substituted and contain in each case 2 to 12 C atoms, in particular 2 to 8 C atoms and preferably 2 to 5 C atoms. Particular preference is given to pentenyl and propinyl. In general, cycloalkyl represents an unsubstituted or substituted cycloalkyl radical having 3 to 10, preferably 3 to 8, C atoms. Particularly preferred cycloalkyl radicals are cyclopropyl, cyclobutyl, cyclopentyl, cyclohexyl and cyclooctyl. In general, aryl represents an unsubstituted or substituted 6- to 10-membered aromatic radical, in particular phenyl. In general, halogen represents fluorine, chlorine, iodine or bromine, in particular fluorine, chlorine or bromine. In general, the term "heterocyclic ring" in the definition of $R^1$ and $R^2$ is to be understood as meaning a substituted or unsubstituted 3- to 10-membered heterocylic ring which is saturated or mono- or polyunsaturated and which contains at least one nitrogen atom and, optionally, 1 to 3 further heteroatoms from the group consisting of N, O and S. The radicals mentioned above are in each case optionally mono- to polysubstituted, preferably mono- to pentasubstituted, in particular mono- to trisubstituted, by identical or different substituents from the group consisting of halogen, $C_1$-$C_{10}$-alkyl, $C_1$-$C_{10}$-halogenoalkyl, $C_1$-$C_{10}$-halogenoalkoxy, phenyl, phenoxy, benzyl or benzyloxy.

Preference is given to using triazolopyrimidine derivatives of the formula (I), in which $R^1$ represents $C_1$-$C_8$-alkyl which is optionally mono- or polysubstituted by identical or different substituents from the group consisting of halogen, phenyl and $C_1$-$C_6$-halogenoalkyl, represents $C_3$-$C_8$-cycloalkyl which is optionally mono- or polysubstituted by identical or different substituents from the group consisting of halogen, $C_1$-$C_6$-alkyl, $C_1$-$C_6$-halogenoalkyl and phenyl, or represents $C_2$-$C_8$-alkenyl or $C_2$-$C_8$-alkinyl, $R^2$ represents hydrogen or $C_1$-$C_8$-alkyl, or $R^1$ and $R^2$ together with the N atom to which they are attached represent a three- to eight-membered heterocyclic ring which is optionally substituted by phenyl or $C_1$-$C_6$-alkyl, $R^3$ represents phenyl which is optionally mono- or polysubstituted by identical or different substituents from the group consisting of halogen, $C_1$-$C_6$-alkyl, $C_1$-$C_4$-halogenoalkyl, $C_1$-$C_6$-alkoxy, $C_1$-$C_4$-halogenoalkoxy, phenyl and phenoxy, $R^4$ represents hydrogen, chlorine, fluorine or bromine.

Particular preference is given to the use of triazolopyrimidine derivatives of the formula (I) in which $R^1$ represents $C_1$-$C_4$-alkyl which is optionally mono- to trisubstituted by identical or different substituents from the group consisting of fluorine, chlorine, bromine and trifluoromethyl, represents $C_3$-$C_8$-cycloalkyl which is optionally mono- to trisubstituted by identical or different substituents from the group consisting of $C_1$-$C_3$-alkyl, fluorine, chlorine, bromine and trifluoromethyl, or represents $C_2$-$C_5$-alkenyl or $C_2$-$C_5$-alkinyl, $R^2$ represents hydrogen or $C_1$-$C_3$-alkyl, or $R^1$ and $R^2$ together with the nitrogen atom to which they are attached represent a five- to seven-membered heterocyclic ring which is optionally substituted by $C_1$-$C_3$-alkyl or phenyl, $R^3$ represents phenyl which is optionally mono- to pentasubstituted by identical or different substituents from the group consisting of halogen, $C_1$-$C_4$-alkyl, $C_1$-$C_3$-alkoxy, $C_1$-$C_2$-halogenoalkyl, $C_1$-$C_2$-halogenoalkoxy, phenyl and phenoxy $R^4$ represents chlorine or bromine.

Very particular preference is given to the use of the compounds of the formula (I) in which $R^1$ represents methyl, ethyl, propyl, trifluoropropyl, 2-(1,1,1-trifluoropropyl), benzyl, pentenyl, propinyl, cyclopropyl, cyclopentyl, trimethylcyclopentyl, cyclohexyl, trimethylcyclohexyl or cyclooctyl, R represents hydrogen, methyl or ethyl, or $R^1$ and $R^2$ together with the nitrogen atom to which they are attached represent piperidyl, phenylpiperidyl, methylpiperidyl or azepinyl, $R^3$ represents phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-chloro-6-fluorophenyl, 2,4-difluorophenyl, 3,4-difluorophenyl, 2,6-difluorophenyl, 2,4,6-trifluorophenyl, 2,3,6-trifluorophenyl, 2,4-dichlorophenyl, 3,4-dichlorophenyl, 2,6-dichlorophenyl, 2,4,6-trichlorophenyl, 2-methylphenyl, 3-methylphenyl, 4-methylphenyl, 2-trifluoromethylphenyl, 3-trifluoromethylphenyl, 4-trifluoromethylphenyl, 3-butylphenyl, 4-butylphenyl, 2-methoxyphenyl, 3-methoxyphenyl, 4-methoxyphenyl, 3-trifluoromethoxyphenyl, 4-trifluoromethoxyphenyl, 3,4-dimethoxyphenyl or 2,6-difluoro-4-methoxyphenyl, and $R^4$ represents chlorine.

The radicals given in the respective definitions or preferred and particularly preferred definitions can be replaced by any radical definitions of other combinations, independently of the combination given in each case. Moreover, radical definitions from a preferred range may not apply.

The present invention also provides the metal salts, the acid addition compounds, the N-oxides and, if a centre of chirality is present, the optionally enriched (R)- and (S) isomers and also their racemates, of the compounds of the general formula (I) as microbicides for protecting engineered materials.

Suitable metal salts are preferably salts of metals of the II. to IV. main group and the I. and II. and the IV. to VIII. transition group of the Periodic System, examples which may be mentioned being copper, zinc, manganese, magnesium, tin, iron, calcium, aluminium, lead, chromium, cobalt and nickel.

Suitable anions of the salts are those which are preferably derived from the following acids: hydrohalic acids, such as, for example, hydrochloric acid and hydrobromic acid, furthermore phosphoric acid, nitric acid and sulfuric acid.

The metal salt complexes of the compounds of the general formula (I) can be obtained in a simple manner by customary processes, such as by dissolving the metal salt in alcohol, e.g., ethanol, and adding the solution to compounds of the general formula (I). The metal salt complexes can be isolated in a known manner, for example by filtration, and, optionally, be purified by recrystallization.

To prepare acid addition compounds of the compounds of the general formula (I), use is preferably made of the following acids: hydrohalic acids, such as hydrochloric acid and hydrobromic acid, in particular hydrochloric acid, furthermore phosphoric acid, nitric acid, sulfuric acid, mono- and bifunctional carboxylic acids and hydroxy-carboxylic acids, such as, for example, acetic acid, propionic acid, 2-ethylhexanoic acid, butyric acid, mandelic acid, oxalic acid, succinic acid, 2-hydroxy-ethane-dicarboxylic acid, maleic acid, fumaric acid, tartaric acid, citric acid, salicylic acid, sorbic acid, lactic acid, and also sulfonic acids, such as, for example, p-toluenesulfonic acid, 1,5-naphthalenedisulfonic acid, alkanesulfonic acids, benzoic acid and, optionally, substituted benzoic acids.

The acid addition salts of compounds of the general formula (I) can be obtained in a simple manner by customary methods for forming salts, for example by dissolving a compound of the general formula (I) in a suitable inert solvent and adding the acid, for example hydrochloric acid, and be isolated in a known manner, for example by filtration, and, optionally, be purified by washing with an inert organic solvent.

Surprisingly, the substances of the formula (I) which can be used according to the invention have potent microbicidal action and can be used for controlling undesirable microorganisms, such as fungi and bacteria, in the protection of materials.

In the protection of materials, the substances according to the invention can be used for protecting engineered materials against attack and destruction by undesirable microorganisms. In the present context, engineered materials are to be understood as meaning non-live materials which have been prepared for use in industry. For example, engineered materials which are intended to be protected by this invention from microbial change or destruction can be glues, sizes, paper and board, textiles, leather, wood, paints and synthetic articles, cooling lubricants and other materials which can be attacked or destroyed by microorganisms. Parts of production plants, for example cooling-water circuits, which may be impaired by the multiplication of microorganisms may also be mentioned in the context of the materials to be protected. Engineered materials which may preferably be mentioned in the context of the present invention are glues, sizes, paper and boards, leather, wood, paints, cooling lubricants and heat transfer liquids.

The active compounds of the formula (I) and the compositions or concentrates comprising them, and also mixtures, are preferably used for protecting wood and timber against microorganisms, e.g., against wood-destroying or wood-discoloring organisms, in particular fungi.

Wood which can be protected by the compounds of the formula (I) or by compositions comprising them is to be understood as meaning, for example, but not exclusively: construction timber, wooden beams, railway sleepers, bridge components, jetties, wooden vehicles, boxes, pellets, containers, telephone poles, wooden fences, wooden claddings, windows and doors made of wood, plywood, chipboard, joiners work or wood-based materials used in domestic construction or in joinery.

Particularly effective protection of wood is achieved by industrial-scale impregnating processes, e.g., vacuum, double-vacuum or pressure processes.

Examples of microorganisms which are capable of bringing about degradation of, or change in, the engineered materials and which may be mentioned are bacteria, fungi, yeasts, algae and slime organisms. The active compounds according to the invention preferably act against fungi, in particular moulds and wood-discoloring and wood-destroying fungi. Microorganisms of the following genera may be mentioned by way of example:
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*,
*Staphylococcus*, such as *Staphylococcus aureus*.

Depending on their particular physical and/or chemical properties, the active compounds of the formula (I) can be converted to the customary formulations, such as solutions, emulsions, suspensions, powders, foams, pastes, granules, aerosols, microencapsulations in polymeric substances, and also ULV cool and warm fogging formulations.

The formulations or compositions for protecting engineered materials are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, notable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are, for example, lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used in a mixture with known fungicides, bactericides, acaricides, nematicides or insecticides, for example to widen the activity spectrum or to prevent the development of resistance. In many cases, synergistic effects are obtained, i.e., the activity of the mixture is greater than the activity of the individual components.

The following co-components are found to be particularly favorable in this context:
triazoles such as: azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazol, penconazole, propioconazole, (±)-cis-1-(4-chlorophenyl)-2-(1H-1,2,4-triazol-1-yl)-cycloheptanol, 2-(1-tert-butyl)-1-(2- chlorophenyl)-3-(1,2,4-triazol-1-yl)-propan-2-ol, tebuconazole, tetraconazole, triadimefon, triadimenol, triapenthenol, triflumizole, triticonazole, uniconazole and their metal salts and acid adducts; imidazoles such as: clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one, and their metal salts and acid adducts;

pyridines and pyrimidines such as: ancymidol, buthiobate, fenarimol, mepanipyrin, nuarimol, pyvoxyfur, triamirol;

succinate dehydrogenase inhibitors such as: benodanil, carboxim, carboxim sulfoxide, cyclafluramid, fenfuram, flutanil, furcarbanil, furmecyclox, mebenil, mepronil, methfuroxam, metsulfovax, pyrocarbolid, oxycarboxin, shirlan, Seedvax;

naphthalene derivatives such as: terbinafine, naftifine, butenafine, 3-chloro-7-(2-aza-2,7,7-trimethyl-oct-3-en-5-ine);

sulfenamides such as: dichlofluanid, tolylfluanid, folpet, fluorofolpet, captan, captofol; benzimidazoles such as: carbendazim, benomyl, fuberidazole, thiabendazole or their salts;

morpholine derivatives such as: aldimorph, dimethomorph, dodemorph, falimorph, fenpropidin fenpropimorph, tridemorph, trimorphamid and their arylsulfonate salts such as, for example, p-toluenesulfonic acid and p-dodecylphenyl-sulfonic acid;

benzothiazoles such as: 2-mercaptobenzothiazole; benzothiophene dioxides such as: N-cyclohexyl-benzo[b]thiophene-S,S-dioxide carboxamide;

benzamides such as: 2,6-dichloro-N-(4-trifluoromethylbenzyl)-benzamide, tecloftalam; boron compounds such as: boric acid, boric ester, borax;

formaldehyde and formaldehyde-releasing compounds such as: benzyl alcohol mono-(poly)-hemiformal, n-butanol hemiformal, dazomet, ethylene glycol hemiformal, hexa-hydro-S-triazine, hexamethylene-tetramine, N-hydroxymethyl-N''-methylthiourea, N-methylolchloro-acetamide, oxazolidine, paraformaldehyde, taurolin, tetrahydro-1,3-oxazine, N-(2-hydroxypropyl)-amine-methanol;

isothiazolinones such as: N-methylisothiazolin-3-one, 5-chloro-N-methylisothiazolin-3-one, 4,5-dichloro-N-octyl-isothiazolin-3-one, 5-chloro-N-octylisothiazolinone, N-octyl-isothiazolin-3-one, 4,5-trimethylene-isothiazolinone, 4,5-benzoisothiazolinone;

aldehydes such as: cinnamaldehyde, formaldehyde, glutardialdehyde, β-bromocinnamaldehyde;

thiocyanates such as: thiocyanatomethylthiobenzothiazole, methylenebisthiocyanate;

quaternary ammonium compounds and guanidines such as: benzalkonium chloride, benzyldimethyltetradecylammonium chloride, benzyldimethyldodecylammonium chloride, dichlorobenzyl-dimethyl-alkyl-ammonium chloride, didecyldimethylammonium chloride, dioctyl-dimethyl-ammonium chloride. N-hexadecyl-trimethyl-ammonium chloride, 1-hexadecyl-pyridinium chloride, iminoctadine tris (albesilate);

iodine derivatives such as: diiodomethyl p-tolyl sulfone, 3-iodo-2-propinyl alcohol, 4-chlorophenyl 3-iodopropargylformate 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;

phenols such as: tribromophenol, tetrachlorophenol, 3-methyl-4-chlorophenol, 3,5-dimethyl-4-chlorophenol, phenoxyethanol, dichlorophene, 2-benzyl-4-chlorophenol, 5-chloro-2-(2,4-dichlorophenoxy)-phenol, hexachlorophene, p-hydroxybenzoate, o-phenylphenol, m-phenylphenol, p-phenylphenol and their alkali metal salts and alkaline earth metal salts;

microbicides with an activated halogen group such as: bronidox, 2-bromo-2-nitro-1,3-propanediol, 2-bromo-4'-hydroxy-aceto-phenone, 1-bromo-3-chloro-4,4,5,5-tetramethyl-2-imidazolidinone, β-brom-β-nitrostyrene, chloracetamid, chloramin T, 1,3-dibromo-4,4,5,5-tetramethyl-2-imidazolidinone, dichloramin T, 3,4-dichloro-(3H)-1,2-dithiol-3-one, 2,2-dibromo-3-nitrile-propionamide, 1,2-dibromo-2,4-dicyanobutane, halane, halazone, mucochloric acid, phenyl (2-chlorocyano-vinyl) sulfone, phenyl (1,2-dichloro-2-cyanovinyl) sulfone, tri-chloroisocyanuric acid;

pyridines such as: 1-hydroxy-2-pyridinethione (and their Na, Fe, Mn, Zn salts), tetrachloro-4-methylsulfonylpyridine, pyrimethanol, mepanipyrim, dipyrithion, 1-hydroxy-4-methyl-6-(2,4,4-trimethylpentyl)-2(1H)-pyridine;

methoxyacrylates or similar such as: azoxystrobin, methyl (E)-methoximino[alpha-(o-tolyloxy)-o-tolyl]acetate, (E)-2-methoxyimino-N-methyl-2-(2-phenoxyphenyl)acetamide, (E)-2-{2-[6-(2-cyanophenoxy)pyrimidin-4-yloxy]phenyl}-3-methoxyacrylate, O-methyl 2-[[[[[3-methoximino-2-butyl]imino]imino]oxy]o-tolyl]-2-methox-imino-acetimidate, 2-[[[[1-(2,5-dimethylphenyl)ethylidene]amino]oxy]methyl]-alpha-(methoximino)-N-methylbenzeneacetamide, alpha-(methoxyimino)-N-methyl-2-[[[[1-[3-(trifluoromethyl)phenyl]ethylidene]amino]oxy]methyl]-benzeneacetamide, trifluoxystrobin, alpha-(methoxymethylene)-2-[[[[1-[3-trifluoromethyl)phenyl]ethylidene]-amino]oxy]methyl]-benzeneacetic acid methyl ester, 2-[[[5-chloro-3-(trifluoromethyl)-2-pyridinyl]oxy]methyl]-alpha-(methoxyimino)-N-methylbenzeneacetamide, 2-[[[cyclopropyl[(4-ethoxyphenyl)imino]methyl]thio]methyl]-alpha-(methoxyimino)-benzeneacetic acid methyl ester, alpha-(methoxyimino)-N-methyl-2-(4-methyl-5-phenyl-2,7-dioxa-3,6-diazaocta-3,5-dien-1-yl)-benzeneacetamide, alpha-(methoxymethylene)-2-(4-methyl-5-phenyl-2,7-dioxa-3,6-diazaocta-3,5-dien-1-yl)-benzeneacetic acid methyl ester, alpha-(methoxyimino)-N-methyl-2-[[[1-[3-(trifluoromethyl)phenyl]ethoxy]-imino]methyl]-benzeneacetamide, 2-[[(3,5-dichloro-2-pyridinyl)oxy]methyl]-alpha-(methoxyimino)-N-methyl-benzeneacetamide, 2-[4,5-dimethyl-9-(4-morpholinyl)-2,7-dioxa-3,6-diazanona-3,5-dien-1-yl]-alpha-(methoxymethylene)-benzeneacetic acid methyl ester, kresoxim-methyl;

metal soaps such as:
tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as:
copper hydroxycarbonate, sodium dichromate, potassium dichromate, potassium chromate, copper sulfate, copper chloride, copper borate, zinc fluorosilicate, copper fluorosilicate;

oxides such as:
tributyltin oxide, Cu2O, CuO, ZnO;

dithiocarbamates such as:
cufraneb, ferban, potassium N-hydroxymethyl-N''-methyl-dithiobarbamate, sodium dimethyldithiocarbamate, potassium dimethyldithiocarbamate, macozeb, maneb, metam, metiram, thiram, zineb, ziram;

nitriles such as:
2,4,5,6-tetrachloroisophthalonitrile, disodium cyano-dithio-imidocarbamate;
quinolines such as:
8-hydroxyquinoline and their copper salts;
other fungicides and bactericides such as:
5-hydroxy-2(5H)-furanone, 4,5-benzodithiazolinone, 4,5-trimethylenedithiazolinone, N-(2-p-chlorobenzoylethyl)-hexaminium chloride, 2-oxo-2-(4-hydroxy-phenyl)acetohydroxamic acid chloride, tris-N-(cyclohexyldiazeniumdioxy)-aluminium, N-(cyclohexyldiazeniumdioxy)-tributyltin or its potassium salts, bis-N-(cyclohexyldiazeniumdioxy)-copper; iprovalicarb, fenhexamid, spiroxamine, carpropamid, diflumetorin, quinoxyfen, famoxadone, polyoxorim, acibenzolar S-methyl, furametpyr, trifluzamide, methalaxy-M, Ag-, Zn- or Cu-containing zeolites alone or incorporated into polymeric materials.

Very especially preferred are mixtures with azaconazole, bromuconazole, cyproconazole, dichlobutrazol, diniconazole, hexaconazole, metaconazole, penconazole, propiconazole, tebuconazole, dichlofluanid, tolylfluanid, fluorfolpet, methfuroxam, carboxin, benzo[b]thiophene S,S-dioxide N-cyclohexylcarboxamide, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methyl-isothiazolin-3-one, N-octylisothiazolin-3-one, dichloro-N-octyliso-thiazolinone, mercaptobenthiazole, thiocyanatomethylthiobenzothiazole, benzoisothiazolinone, N-(2-hydroxypropyl)-amino-methanol, benzyl alcohol (hemi)-formal, N-methylolchloroacetamide, N-(2-hydroxypropyl)-amine-methanol, glutaraldehyde, omadine, dimethyl dicarbonate, 2-bromo-2-nitro-1,3-propanediol and/or 3-iodo-2-propinyl n-butylcarbamate.

Apart from with the abovementioned fungicides and bactericides, mixtures with a good efficacy are, moreover, also prepared with other active compounds:
insecticides/acaricides/nematicides:
abamectin, acephate, acetamiprid, acrinathrin, alanycarb, aldicarb, aldoxycarb, aldrin, allethrin, alpha-cypermethrin, amitraz, avermectin, AZ 60541, azadirachtin, azinphos A, azinphos M, azocyclotin,
*Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bromophos A, bromophos M, bufencarb, buprofezin, butathiophos, butocarboxim, butoxycarboxim,
cadusafos, carbaryl, carbofuran, carbophenothion, carbosulfan, cartap, quinomethionate, cloethocarb, chlordane, chlorethoxyfos, chlorfenapyr, chlorfenvinphos, chlorfluazuron, chlormephos, N-[(6-chloro-3-pyridinyl)-methyl]N'-cyano-N-methyl-ethaneimidamide, chlorpicrin, chlorpyrifos A, chlorpyrifos M, cis-resmethrin, clocythrin, cypophenothrin clofentezin, coumaphos, cyanophos, cyproprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1-(1,1-dimethyl)-hydrazine, DNOC, dichlofenthion, dichlorvos, dicliphos, dicrotophos, difethialone, diflubenzuron, dimethoate, dimethyl-(phenyl)-silyl-methyl 3-phenoxybenzyl ether, dimethyl-(4-ethoxyphenyl)-silylmethyl-3-phenoxybenzyl ether, dimethylvinphos, dioxathion, disulfoton, eflusilanate, emamectin, empenthrin, endosulfan, EPN, esfenvalerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximat, fensulfothion, fenthion, fenvalerate, fipronil, fluazuron, flucycloxuron, flucythrinate, flufenoxuron, flupyrazofos, flufenzine, flumethrin, flufenprox, fluvalinate, fonophos, formethanate, formothion, fosmethilan fosthiazate, fubfenprox, furathiocarb, halofenocid. HCH, heptenophos, hexaflumuron, hexythiazox, hydramethylnon, hydroprene, imidacloprid, imiprothrin, indoxycarb, iodfenfos, iprinomectin, iprobenfos, isazophos, isoamidophos, isofenphos, isoprocarb, isoprothiolane, isoxathion, ivermectin, lama-cyhalothrin, lufenuron, kadedrinlambda-cyhalothrin, lufenuron, malathion, mecarbam, mervinphos, mesulfenphos, metaldehyde, methacrifos, methamidophos, methidathion, methiocarb, methomyl, metalcarb, milbemectin, monocrotophos, moxiectin, naled, NC 184, NI 125, nicotine, nitenpyram, omethoate, oxamyl, oxydemethon M, oxydeprofos, parathion A, parathion M, penfluoron, permethrin, 2-(4-phenoxyphenoxy)-ethyl ethylcarbamate, phenthoate, phorate, phosalon, phosmet, phosphamidon, phoxim, pirimicarb, pirimiphos M, pirimiphos A, prallethrin, profenophos, promecarb, propa-phos, propoxur, prothiophos, prothoate, pymetrozin, pyrachlophos, pyridaphenthion, pyresmethrin, pyrethrum, pyridaben, pyrimidifen, pyriproxifen, pyrithiobac-sodium, quinalphos, resmethrin, RH-7988, rotenone, salithion, sebufos, silafluofen, spinosad, sulfotep, sulprofos, tau-fluvalinate, taroils, tebufenozide, tebufenpyrad, tebupirimphos, teflubenzuron, tefluthrin, temephos, terbam, terbufos, tetrachlorvinphos, tetramethrin, Tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, trichlorfon, triflumuron, trimethacarb,
vamidothion, XMC, xylylcarb, zetamethrin;
molluscicides:
fentin acetate, metaldehyde, methiocarb, niclosamide;
herbicides and other algicides such as
acetochlor, acifluorfen, aclonifen, acrolein, alachlor, alloxydim, ametryn, amidosulfuron, amitrole, ammonium sulfamate, anilofos, asulam, atrazine, azafenidin, aziptrotryne, azimsulfuron, benazolin, benfluralin, benfuresate, bensulfuron, bensulfide, bentazone, benzofencap, benzthiazuron, bifenox, bispyribac, bispyribac-sodium, bispyribac-methyl, borax, bromacil, bromobutide, bromofenoxim, bromoxynil, butachlor, butamifos, butralin, butylate, bialaphos, benzoylprop, bromobutide, butroxydim,
carbetamide, carfentrazone-ethyl, carfenstrole, chlomethoxyfen, chloramben, chlorbromuron, chiorflurenol, chloridazon, chlorimuron, chlornitrofen, chloroacetic acid, chioransulam-methyl, cinidon-ethyl, chlorotoluron, chloroxuron, chlorpropham, chlorsulfuron, chlorthal, chlorthiamid, cinmethylin, cinofulsuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyclosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichiobenil, dimethamid, dithiopyr, dimethametryn, eglinazine, endothal, EPIC, esprocarb, ethaifluralin, ethidimuron, ethofumesate, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchioralin, flufenacet, flumeturon, fluorocglycofen, fluoronitrofen, flupropanate, flurenol, fluridone, fluorochloridone, fluoroxypyr, fomesafen, fosamine, fosametine, flamprop-isopropyl, flamprop-isopropyl-L, flumiclorac-pentyl, flumipropyn, flumioxzim, flurtamone, flumioxzim, flupyrsulfuron-methyl, fluthiacet-methyl, glyphosate, glufosinate-ammonium haloxyfop, hexazinone, imazamethabenz, isoproturon, isoxaben, isox-apyrifop, imazapyr, imazaquin, imazethapyr, ioxynil, isopro-palin, imazosulfuron, imazomox, isoxaflutole, imazapic, lactofen, lenacil, linuron, MCPA, MCPA-thioethyl, MCPB, mecoprop, mecoprop-P, mefenacet, mefluidide, metam, metamitron, metazachlor, methabenzthiazuron, methazole, methoropytryne, methyldymron, methyl isothiocyanate, metobromuron, metoxuron, metribuzin, metsulfuron, moli-nate, manolide, monolinuron, MSMA, metolachior, metosu-lam, metobenzuron, naproanilide, napropamide, naptalam, neburon, nicosulfuron, norflurazon, sodium chlorate, oxadia-zon, oxyfluorfen, oxysulfuron, orbencarb, oryzalin, oxadiar-gyl, propyzamide, prosulfocarb, pyrazolate, pyrazolsulfuron, pyrazoxyfen, pyribenzoxium, pyributicarb, pyridate, paraquat, pebulate, pendimethalin, pentachlorophenol, pen-toxazone, pentanochlor, petroleum oils, phenmedipham, picloram, piperophos, pretilachlor, primisulfuron, prodi-amine, prometryn, propachlor, propanil, propaquizafob, pro-pazine, propham, proisochlor, pyriminobac-methyl, pelar-gonic acid, pyrithiobac, pyraflufen-ethyl, quinmerac, quinocloamine, quizalofop, quizalofop-P, quinchlorac, rimsulfuron sethoxydim, sifuron, simazine, simetryn, sulfosulfuron, sulfometuron, sulfentrazone, sulcot-rione, sulfosate, tar oils, TCA, tebutam, tebuthiuron, terbacil, terbumeton, terbuthylazine, terbutryn, thiazafluoron, thifen-sulfuron, thiobencarb, thiocarbazil, tralkoxydim, tri-allate, triasulfuron, tribenuron, triclopyr, tridiphane, trietazine, trif-luoralin, tycor, thdiazimin, thiazopyr, triflusulfuron, verno-late.

The active compounds can be used as such, in the form of concentrates or in the form of their formulations or the use forms prepared therefrom, such as ready-to-use solutions, suspensions, wettable powders, pastes, soluble powders, dusts and granules.

The compositions used for protecting engineered materials generally comprise the active compounds in an amount of from about 1 to about 95%, preferably from about 10 to about 75%.

The use concentrations of the active compounds according to the invention depend on the type and the occurrence of the microorganisms to be controlled, and on the composition of the material to be protected. The optimal rate can be deter-mined by test series. In general, the use concentrations are in the range from about 0.001 to about 5% by weight, preferably from about 0.05 to about 1.0% by weight, based on the mate-rial to be protected.

The invention is further described in the following illustra-tive examples in which all parts and percentages are by weight unless otherwise indicated.

EXAMPLES

Use Example

Inhibitory test with giant colonies of Basidiomycetes

Mycelium pieces were punched out of colonies of Gloeo-phyllum trabeum (P1), Coniophora puteana (P2), *Poria* pla-centa (P3), *Lentinus* tigrinus (P4), *Coriolus versicolor* (P5) and Sterum sanguinolentum (P6) and incubated at 26° C. on an agar medium. The inhibition of the growth of the fungal threads on the active-compound-containing medium (con-centration of active compound: 6 ppm) was compared to the longitudinal growth of medium without added active com-pound and rated in inhibition percent.

Table 1 shows the results.

TABLE 1

| No | R1 | R2 | R3 | R4 | P1 | P2 | P3 | P4 | P5 | P6 |
|----|----|----|----|----|----|----|----|----|----|----|
| 1 | Cyclopentyl | H | 3-fluoro-phenyl | Cl | 80 | 100 | | | 91 | |
| 2 | Cyclopentyl | H | 2-chloro-phenyl | Cl | 100 | 100 | | 94 | 100 | 100 |
| 3 | Cyclopentyl | H | 2,6-difluoro-phenyl | Cl | 100 | 100 | | 100 | 100 | 100 |
| 4 | Cyclopentyl | H | 2,4,6-tri-fluoro-phenyl | Cl | | | | | 100 | |
| 5 | Cyclopentyl | H | pPhenyl | Cl | | | | | 100 | |
| 6 | Isopropyl | H | 2,4-di-chloro-phenyl | Cl | 95 | 100 | | | 95 | 100 |
| 7 | —(CH$_2$)$_6$— | | 2-fluoro-phenyl | Cl | 100 | 100 | | 94 | 100 | 100 |
| 8 | —(CH$_2$)$_6$— | | 2,6-di-fluoro-phenyl | Cl | 100 | 100 | 100 | 100 | 100 | 100 |
| 9 | —(CH$_2$)$_2$CHCH$_3$(CH$_2$)$_2$— | | 2,4,6-tri-fluoro-phenyl | Cl | 100 | 100 | 100 | 100 | 100 | 100 |
| 10 | —(CH$_2$)$_2$CHCH$_3$(CH$_2$)$_2$— | | 2-chloro-6-fluoro-phenyl | Cl | 100 | 100 | 100 | 100 | 100 | 100 |
| 11 | (S)-2-(1,1,1-trifluoro)-propyl | H | 2,4,6-tri-fluoro-phenyl | Cl | 100 | 100 | 100 | 100 | 100 | 100 |

What is claimed is:

1. A microbicidal composition comprising:
at least one compound of the formula (I)

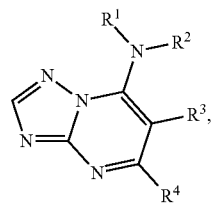

wherein
R¹ represents methyl, ethyl, propyl, benzyl, pentenyl, propinyl, cyclopropyl, cyclopentyl, trimethylcyclopentyl, cyclohexyl, trimethylcyclohexyl or cyclooctyl,
R² represents hydrogen, methyl or ethyl, or
R¹ and R² together with the nitrogen atom to which they are attached represent piperidyl, phenylpiperidyl, methylpiperidyl or azepinyl,
R³ represents phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-chloro-6-fluorophenyl, 2,4-difluorophenyl, 3,4-difluorophenyl, 2,6-difluorophenyl, 2,4,6-trifluorophenyl, 2,3,6-trifluorophenyl, 2,4-dichlorophenyl, 3,4-di-chlorophenyl, 2,6-dichlorophenyl, 2-methylphenyl, 3-methylphenyl, 4-methylphenyl, 3-butylphenyl, 4-butylphenyl, 2-methoxyphenyl, 3-methoxyphenyl, 4-methoxyphenyl, 3-trifluoromethoxyphenyl, 4-trifluoromethoxyphenyl, 3,4-dimethoxyphenyl or 2,6-difluoro-4-methoxyphenyl, and
R⁴ represents chlorine, and
at least one solvent or diluent.

2. The composition according to claim 1, further comprising:
at least one further antimicrobially active compound selected from the group consisting of fungicides, bactericides, acaricides, nematicides, insecticides, and combinations thereof.

3. The composition according to claim 1, wherein R¹ is cyclopentyl.

4. The composition according to claim 1, wherein at least one compound of the formula (I) is 5-chloro-7-(4-methylpiperidin-1-yl)-6-(2,4,6-trifluorophenyl)-[1,2,4]triazolo[1,5-a]pyrimidine, as represented by

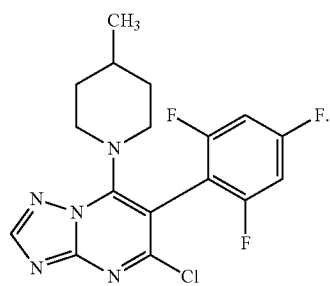

* * * * *